US008433711B2

(12) United States Patent
Odom et al.

(10) Patent No.: US 8,433,711 B2
(45) Date of Patent: Apr. 30, 2013

(54) SYSTEM AND METHOD FOR NETWORKED DECISION MAKING SUPPORT

(75) Inventors: Paul S. Odom, Charlotte, NC (US); Robert D. Way, Tiki Island, TX (US)

(73) Assignee: Kang Jo Mgmt. Limited Liability Company, Wilmington, DE (US)

( * ) Notice: Subject to any disclaimer, the term of this patent is extended or adjusted under 35 U.S.C. 154(b) by 1254 days.

(21) Appl. No.: 11/222,046

(22) Filed: Sep. 9, 2005

(65) Prior Publication Data
US 2007/0061128 A1    Mar. 15, 2007

(51) Int. Cl.
G06F 7/00    (2006.01)
G06F 17/30    (2006.01)

(52) U.S. Cl.
USPC ............................ 707/748; 707/723; 707/706

(58) Field of Classification Search ........................ None
See application file for complete search history.

(56) References Cited

U.S. PATENT DOCUMENTS

| | | | |
|---|---|---|---|
| 6,550,055 B1 * | 4/2003 | Cohen et al. .................. 717/124 |
| 6,553,372 B1 * | 4/2003 | Brassell et al. ..................... 707/5 |
| 6,571,240 B1 * | 5/2003 | Ho et al. ............................ 707/5 |
| 7,340,466 B2 | 3/2008 | Odom et al. |
| 2001/0007987 A1 * | 7/2001 | Igata ................................. 707/3 |
| 2002/0023144 A1 * | 2/2002 | Linyard et al. ................ 709/218 |
| 2002/0165856 A1 * | 11/2002 | Gilfillan et al. .................... 707/3 |
| 2002/0169764 A1 * | 11/2002 | Kincaid et al. .................... 707/3 |
| 2003/0018629 A1 * | 1/2003 | Namba .............................. 707/3 |
| 2003/0163302 A1 * | 8/2003 | Yin .................................. 704/9 |
| 2003/0177413 A1 * | 9/2003 | Pillutla et al. .................. 714/25 |
| 2004/0044559 A1 * | 3/2004 | Malik et al. ..................... 705/10 |
| 2004/0054691 A1 * | 3/2004 | Sharma et al. ............. 707/104.1 |
| 2004/0117352 A1 * | 6/2004 | Schabes et al. .................... 707/3 |
| 2004/0122816 A1 * | 6/2004 | Kirkland et al. ................... 707/5 |
| 2005/0138003 A1 * | 6/2005 | Glover et al. ...................... 707/3 |
| 2005/0187919 A1 * | 8/2005 | Takahashi et al. ................. 707/3 |
| 2005/0203888 A1 * | 9/2005 | Woosley et al. ................... 707/3 |
| 2005/0203970 A1 * | 9/2005 | McKeown et al. ............ 707/203 |
| 2006/0022048 A1 * | 2/2006 | Johnson ..................... 235/462.1 |
| 2006/0106778 A1 * | 5/2006 | Baldwin ........................... 707/3 |
| 2006/0184566 A1 * | 8/2006 | Lo et al. ........................ 707/102 |
| 2007/0043761 A1 * | 2/2007 | Chim et al. ................... 707/102 |
| 2007/0185826 A1 * | 8/2007 | Brice et al. ........................ 707/1 |

OTHER PUBLICATIONS

W3C, "XML Path Language (XPath) Version 1.0", Nov. 1999, W3C.*
Simpson, "XPath and XPointer", Jul. 31, 2002, OReilly Media.*
McManus et al., "C# Developers Guide to ASP.NET, XML, and ADO.NET", Mar. 29, 2002, Addison-Wesley Professional.*
Raman, "XForms: XML Powered Web Forms", Sep. 23, 2003, Addison-Wesley Professional.*
Long, NPL "Google Hacking for Penetration Testers", Jul. 2004, Syngress.*

* cited by examiner

*Primary Examiner* — Rehana Perveen
*Assistant Examiner* — Huen Wong

(57) ABSTRACT

The present invention provides systems and methods for decision making support. The decision making support can be used, for example, for help desk troubleshooting, medical diagnosis, financial planning, and expert device. The decision support system of the invention includes a processor and a memory having a decision support program module, a phase dictionary, one or more solution nodes and optionally a topic identification information module. The decision support module is configured to enable the processor to receive a problem constraint and one or more user-specified phrases, which are then used to search nodes in a solution domain to identify a set of nodes potentially related to the user's problem or question. The set of nodes potentially related to the user's problem or question are ranked and displayed. Methods to determine potential solution nodes and to update solution nodes within the decision support system are provided.

20 Claims, 13 Drawing Sheets

Search: Web Pages

500 no sound  [Search] [Reset] [Advanced Search]

Problems:
☐ problem no sound

Questions:
☐ pci sound card
☐ isa sound card
☐ built in sound hardware
☐ has sound card
☐ legacy sound card
☐ plug and play sound card

Diagnostics:
☐ volume level audible
☐ sound card in correct slot
☐ pnp bios configured correctly
☐ supported sound card
☐ compatable legacy driver
☐ compatable pnp bios version
☐ speakers working 450h Is Configuration of BIOS Correct?

A sound card will not be recognized by your computer if the BIOS is not configured correctly. For details on how to configure your BIOS, see your computer manuals..

Does sound card work after BIOS correctly configured?  — 554

○ pnp bios misconfigured
○ pnp bios configured correctly      555
◉ Skip this and try something else.

[Search]

Search: Web Pages

[no sound] [Search] [Reset] [Advanced Search]

Problems:
☐ problem no sound

Questions:
☐ pci sound card
☐ isa sound card
☐ built in sound hardware
☐ has sound card
☐ legacy sound card
☐ plug and play sound card

Diagnostics:
☐ volume level audible
☐ sound card in correct slot
☐ pnp bios configured correctly
☐ supported sound card
☐ compatable legacy driver
☐ compatable pnp bios version
☐ speakers working

*450d*

Does Computer Have Plug and Play Sound Card?

Plug and play sound cards provide the capability for a computer to automatically configure itself to play sound with these cards. Certain operating systems detect plug and play sound cards and install the appropriate drives. However, hardware conflicts are still possible. Consult the manuals associated with the sound card to determine its ty Does computer have plug and play sound card?                    654

○ legacy sound card
○ plug and play sound card     } 655
◉ Skip this and try something else.

[Search]

FIG. 6

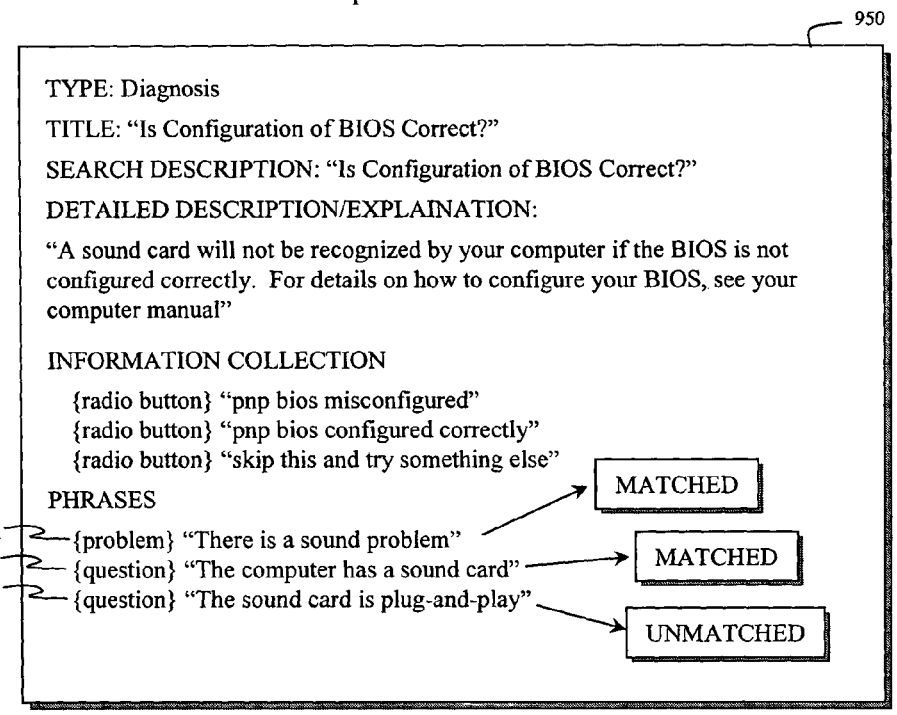
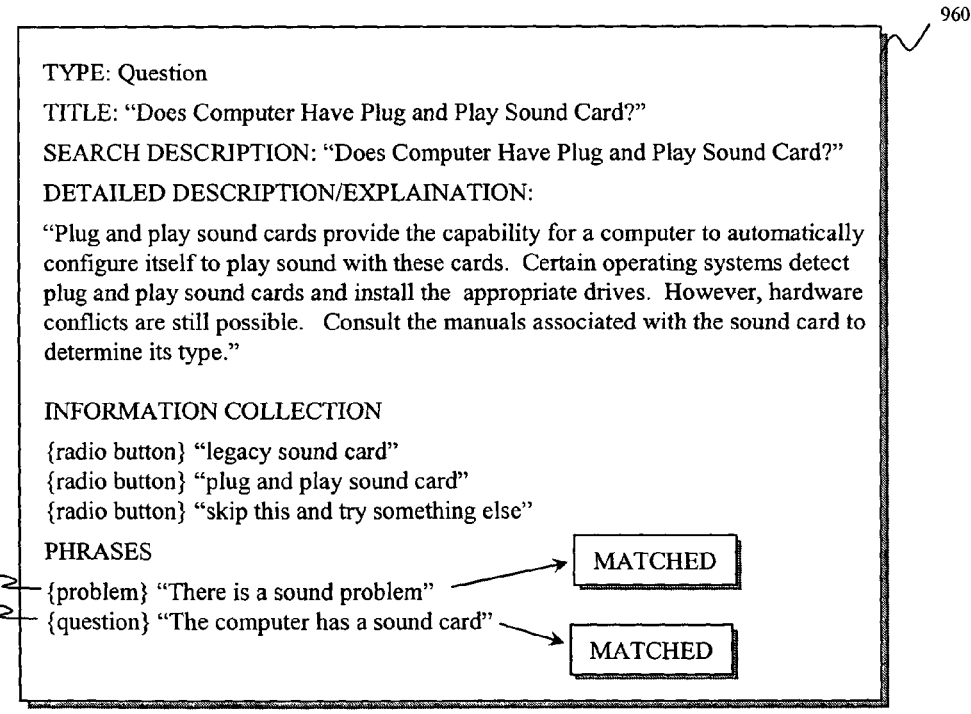
FIG. 9

1300

Search: Web Pages
[no sound] [Search] [Reset] [Advanced Search]
↳ 1305

Selected:
1334 ☑ speakers working OR built in sound hardware OR problem no sound ↳ 1332

Page Identifier ⌐1310

Title: ⌐1320

Short Description ⌐1335

Diagnostics:
☐ volume level audible

☐ no hardware conflict

1330

Detail Body: ⌐1340

Def  Topic Phrases
○
○                                                              } 1350
◉   Question |
              ↳ 1360
[Insert]

FIG. 13

SYSTEM AND METHOD FOR NETWORKED DECISION MAKING SUPPORT

FIELD OF THE INVENTION

The present invention relates generally to data processing systems, and more specifically to decision support systems.

BACKGROUND

Decision support systems such as troubleshooting and diagnosis systems have become integral tools for corporations, researchers, and individuals. Many corporations have established help desks to respond to user problems with software, hardware, or individual products. Other types of help desk and diagnosis systems such as medical diagnosis, financial planning, and the like have also been established to facilitate customer decision making. Customers expect help desk personnel or diagnosis systems to resolve their problems or provide solutions rapidly and efficiently. Unnecessary or repetitive questions increase customer frustration and negatively impact customer satisfaction.

Many computer-based systems have been developed to assist help-desk personnel, users, or employees to identify solutions based on their observations of attributes associated with the problem. In general, decision support systems such as troubleshooting systems and diagnosis systems include a set of questions, potential (differential) diagnoses, and suggestions for how to proceed in order to remedy the diagnosed problem. Typical methodologies employed in these systems include decision trees and Bayesian networks. The primary difference between systems based upon a decision tree approach and those based upon Bayesian networks is in the method used for selection and ordering of questions to be presented to the user.

Decision trees typically use a static hierarchical ordering of questions. This static ordering makes decision trees simple to explain and implement. However, decision trees often become difficult to maintain and update because of the extensive duplication of questions needed for completeness.

Bayesian networks attempt to minimize the number of questions asked during a differential diagnosis by using probabilistic relationships between the different questions. The probabilistic relationships between problem symptoms identified by the user aid in minimizing the solution path. However, Bayesian network systems are typically difficult to implement because the physical characteristics of the system are not probabilistic and they create entirely different solution paths. The maintenance is also problematic because of the amount of data that is necessary to establish the real world probabilities for any new knowledge that must be added to the Bayesian network.

In conventional decision support systems, the onus is placed on the user to understand the problem language and the solution structure implemented by the system. For example, in most systems, problem areas are identified individually; and therefore, the user has to recognize which problem area is appropriate for the problem. In addition, a user must re-interpret the problem using the syntax of the system. Because of these constraints, the intuitive nature of conventional decision support systems is poor, making them impractical for use by end-user customers.

Furthermore, conventional systems force the user to take a particular path to a solution. For example, a user may have to go through multiple steps to arrive at a solution. These multiple steps may involve answering questions which are irrelevant to the problem being addressed.

Another difficulty faced by conventional decision support systems relates to adding new information into the system. In many conventional systems, updates to system information are handled off-line. For example, when new information or a new solution is identified by a system employee or a knowledge worker, that information is sent to an administrator for entry into the system. Thus, the availability of new information in these systems is dependent upon the efficiency of the administrator.

Because Bayesian networks are monolithic, adding new information to the network is challenging. New information must be fully integrated with all the information already in the network. Thus, the new information may not be available to solve user problems for an extended period of time.

What is needed is a decision support system which rapidly converges on a solution and allows a user to take multiple paths to a solution.

What is further needed is a decision support system in which new information can be incrementally added in real-time and immediately integrated into the system.

BRIEF SUMMARY OF THE INVENTION

The present invention is directed to a system and method for networked decision making support. In accordance with an aspect of the present invention, a decision support system includes one or more solution domains, each domain including multiple nodes. A solution domain defines the knowledge area covered by nodes. For example, domains associated with computer technology include computer hardware, computer software, a specific application or tool, or a specific device.

The decision support system receives a user supplied constraint and searches the nodes in the solution domain to generate a first set of nodes which are potentially related to the user's problem. The constraint is one or more words which relate to the user's problem or a diagnostic need. Each node in the first set of potentially related nodes includes the constraint (or a semantic equivalent) in the text of the node. The decision support system generates a phrase list containing one or more phrases from the nodes in the first set of potentially related nodes.

The phrases can be divided into logical groups for presentation purposes to simplify the user's review. For example, presentation categories could be Problem Statement Phrases, Physical Characteristic Phrases, or Diagnosis Phrases. One or more of these phrases can be selected from the phrase list. In addition or alternately the phrases can be indirectly selected from the set of responses associated with an individual solution node when it is selected by the user.

The decision support system then searches the nodes in the solution domain to generate a second set of potentially related nodes. Each node in the second set of potentially related nodes includes the constraint and any of the phrases.

In accordance with a further aspect of the present invention, the decision support system receives a constraint and one or more user-specified phrases. The decision support system then identifies the inverse for each of the user-specified phrases. The decision support system then searches the nodes in the solution domain using the user's constraint, the user-specified phrases, and the inverse of the user-specified phrases to generate a first set of nodes potentially related to the user's problem.

In accordance with a further aspect of the present invention, the nodes are ranked. For each node, the decision support system determines the number of node phrases that match any of the specified phrases and the number of node phrases that do not match any of the specified phrases. The number of matched phrases is multiplied by a first weight to generate a matched value and the number of unmatched phrases is multiplied by a second weight to generate an unmatched value. The unmatched value is subtracted from the matched value to produce a weighted score for the node. Nodes are then ranked according to their weighted score.

In accordance with an additional aspect of the invention, a decision support system includes a memory and a processor. The memory includes one or more nodes, a phrase dictionary, and a decision support module. The decision support module is configured to enable the processor to receive a constraint and one or more user-specified phrases and to search the nodes in the solution domain to identify a set of nodes potentially related to the user's problem. Each node in the set of potentially related nodes includes the constraint and any of the specified phrases and the inverses of the phrases. The decision support module is further configured to enable the processor to rank the solutions in the set of potentially related nodes. In addition, the decision support module is configured to receive additional specified phrases and to search the nodes in the solution domain to identify a set of nodes potentially related to the user's problem using the constraint, the specified phrases previously entered, and the additional specified phrases.

These and other advantages and features will become readily apparent in view of the following detailed description of the invention. Note that the Summary and Abstract sections may set forth one or more, but not all exemplary embodiments of the present invention as contemplated by the inventor.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

FIG. 5 depicts an exemplary screen shot of a diagnosis node display page, according to an embodiment of the present invention.

FIG. 6 depicts an exemplary screen shot of a question node display page, according to an embodiment of the present invention.

FIG. 9 depicts an exemplary decision support system investigation, according to an embodiment of the present invention.

FIG. 13 is an exemplary screen shot of a node entry page, according to an embodiment of the present invention.

Figure 1:
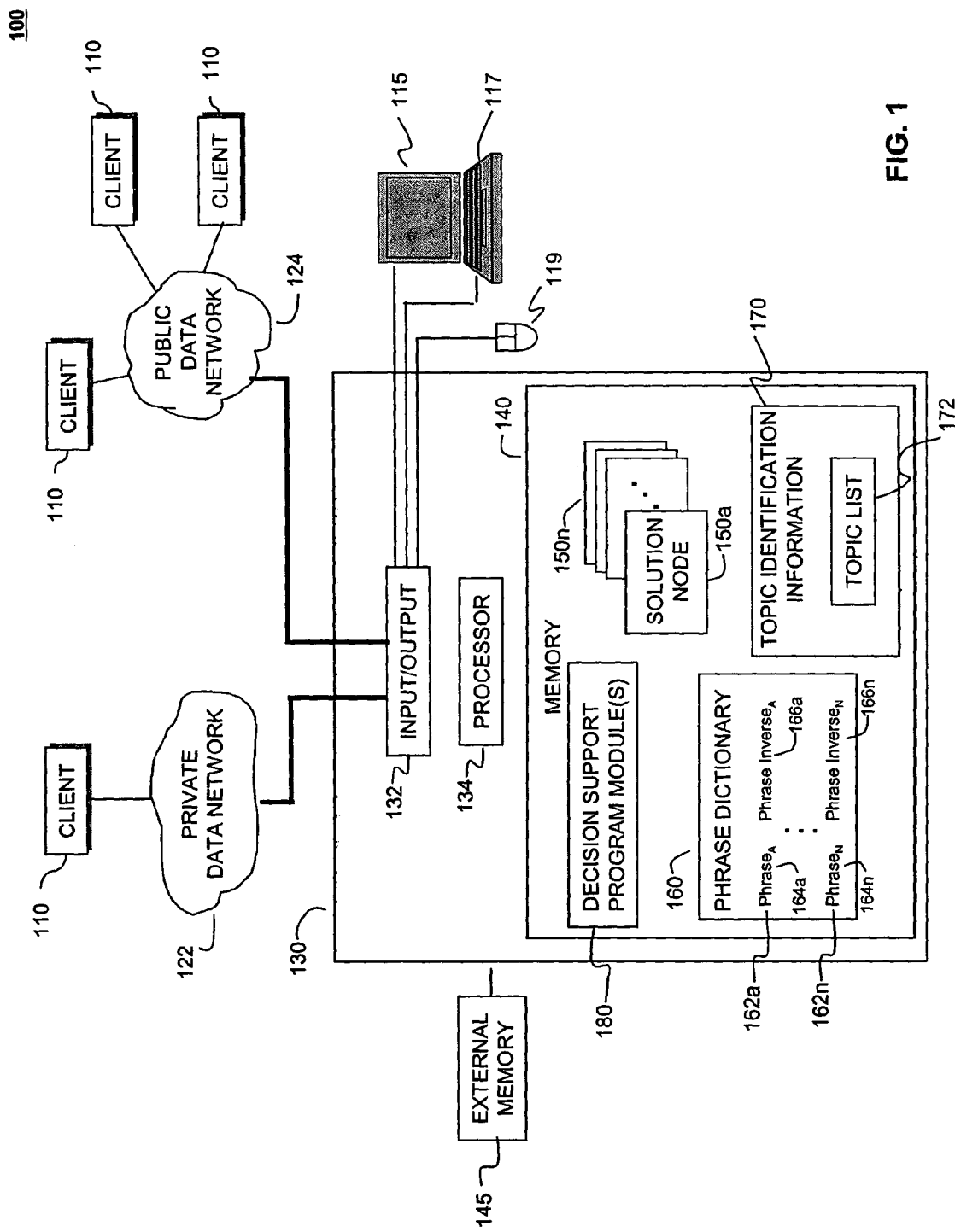
FIG. 1 illustrates an exemplary operating environment for a decision support system, according to an embodiment of the present invention.

The present invention will now be described with reference to the accompanying drawings. In the drawings, like reference numbers can indicate identical or functionally similar elements. Additionally, the left-most digit(s) of a reference number may identify the drawing in which the reference number first appears.

DETAILED DESCRIPTION OF THE INVENTION

1. Decision Support System

FIG. 1 illustrates an exemplary operating environment 100 for the decision support system 130, according to an embodiment of the invention. In addition to troubleshooting technical or other problems encountered by a user, the decision support system 130 of the present invention can be used to aid medical diagnoses or provide expert advice in areas such as tax preparation, repair procedures, or construction material selection, among other areas.

In an embodiment, decision support system 130 is implemented on a general purpose computer. As would be appreciated by persons of skill in the art, decision support system 130 can be implemented on a variety of computer platforms including conventional personal computers, conventional servers, networked personal computers, mainframe computers, hand-held devices, and the like.

In an embodiment, decision support system 130 is a centralized server which is accessed by one or more clients 110 over a private data network 122 such as a Local Area Network (LAN) or over a public data network 124 such as a Wide Area Network (WAN), including the Internet. In addition or alternatively, decision support system 130 could be accessed directly via one or more input devices (e.g., keyboard 117 and mouse 119).

In a help desk environment, a help desk employee may interact with an end user customer via conventional means such as telephone or e-mail to obtain details related to the customer's problem or question. The help desk employee then provides this information to decision support system 130. If decision support system 130 is centralized, the help desk employee enters the information at her client system which transmits the information to decision support system 130 over a private LAN, such as private data network 122.

In addition, a decision support system provider may allow end-user customers to access decision support system 130 directly, without having to interact with a help desk employee. In this configuration, an end-user customer enters information related to his question or problem into a client system which transmits the data to decision support system 130 over a public data network 124. In an additional operating environment, an end-user customer may install decision support system 130 on his personal computer.

For ease of description, a person or system that interacts with decision support system directly (e.g., entering information, viewing results) is referred to as a user. A person that interacts with a user, for example, a help desk representative, to provide information, and does not directly interact with the decision support system, is referred to as an end-user customer.

Decision support system 130 includes input/output system 132, a processor 134, and a memory 140. Input/output system 132 includes components which allow system 130 to communicate with external systems and devices. Memory 140 includes read only memory (ROM) and random access memory (RAM). Memory 140 may also include a hard disk, a magnetic disk, an optical disk, flash memory card, digital video disc (DVD), or any similar type of storage media.

Memory 140 stores decision support program module 180, one or more solution nodes 150a-150n, a phrase dictionary 160, and topic identification information 170. Decision support program module 180 includes a set of computer-executable instructions to be executed on processor 134.

Phrase dictionary 160 includes a plurality of entries 162a-162n. Each entry includes a phrase 164 and its associated inverse 166.

Topic identification information 170 includes topic list 172 and any data required to generate topic list 172. Topic identification information is optional. Topic list 172 includes topics which occur a statistically significant number of times in one or more solution nodes 150a-150n. In general, a topic is an expression of subject matter. A topic may be a word or combination of two or more words. In an embodiment, a topic list entry includes associated frequency data. Frequency data indicates the frequency that a topic occurs in one or more solution nodes. For a more detailed description of topics and topic generation involving two or more words, see U.S. patent application Ser. No. 10/086,026, entitled "Topic Identification and Use Thereof in Information Retrieval Systems."

As would be appreciated by persons of skill in the art, one or more of the data or program modules stored in memory 140 could be stored in a memory 145 external to decision support system 130. In this embodiment, decision support system 130 accesses external memory unit 145 as needed to retrieve data or program modules.

Figure 2A:
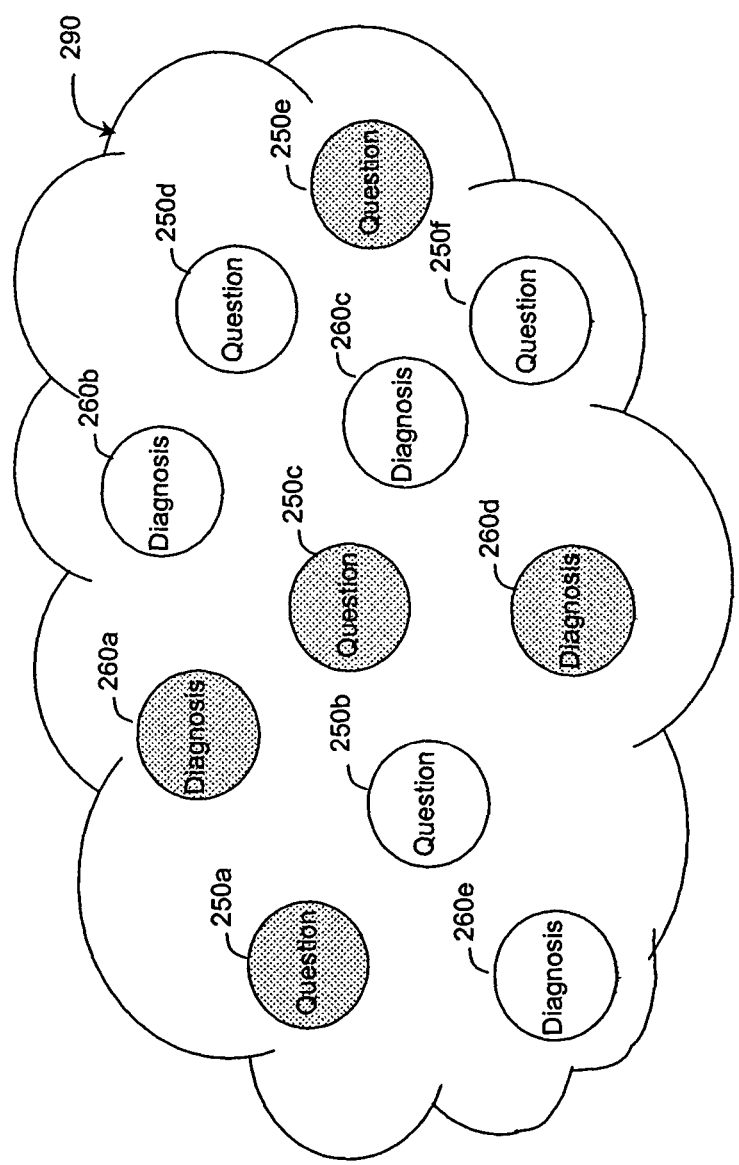
FIG. 2A depicts an exemplary domain, according to an embodiment of the present invention.

Referring to FIG. 2A, in an embodiment of the present invention, decision support system 130 supports one or more solution domains 290. A solution domain 290 defines the knowledge area covered by informational nodes 250a-250n. A domain can cover any knowledge area. For example, in the area of computer technology, computer hardware and computer software may be solution domains. In addition, a domain may be defined for a specific application, specific device, or a category of devices (e.g., cell phones). FIG. 2A depicts an exemplary domain 290, according to an embodiment of the present invention. Domain 290 includes a set of informational nodes 250. In an embodiment, an informational node may be either an question node 250a-250f or a diagnosis node 260a-260e.

After entry of problem constraints by a user, decision support system 130 identifies a subset of the nodes that potentially relate to the defined problem. Nodes potentially related to the problem are shaded in FIG. 2A. A list of the potentially related nodes is presented to the user via a results display page.

Figure 2B:
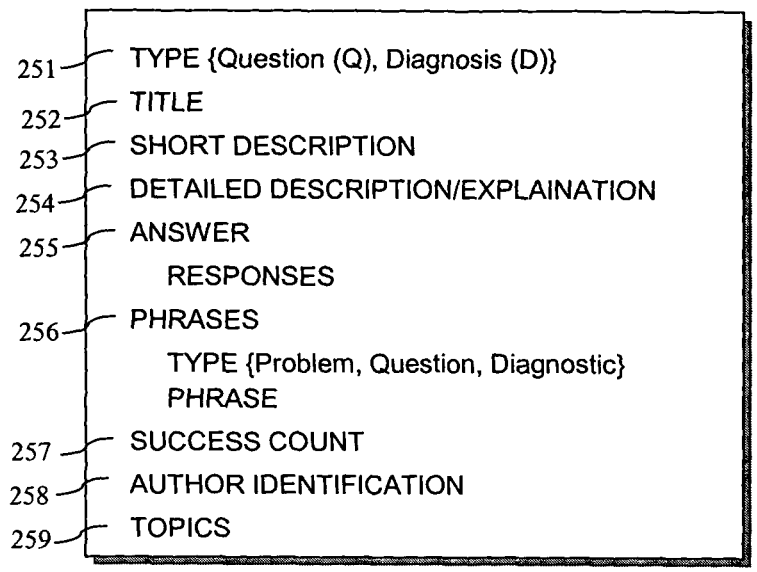
FIG. 2B depicts an exemplary node, according to an embodiment of the present invention.
Figure 4:
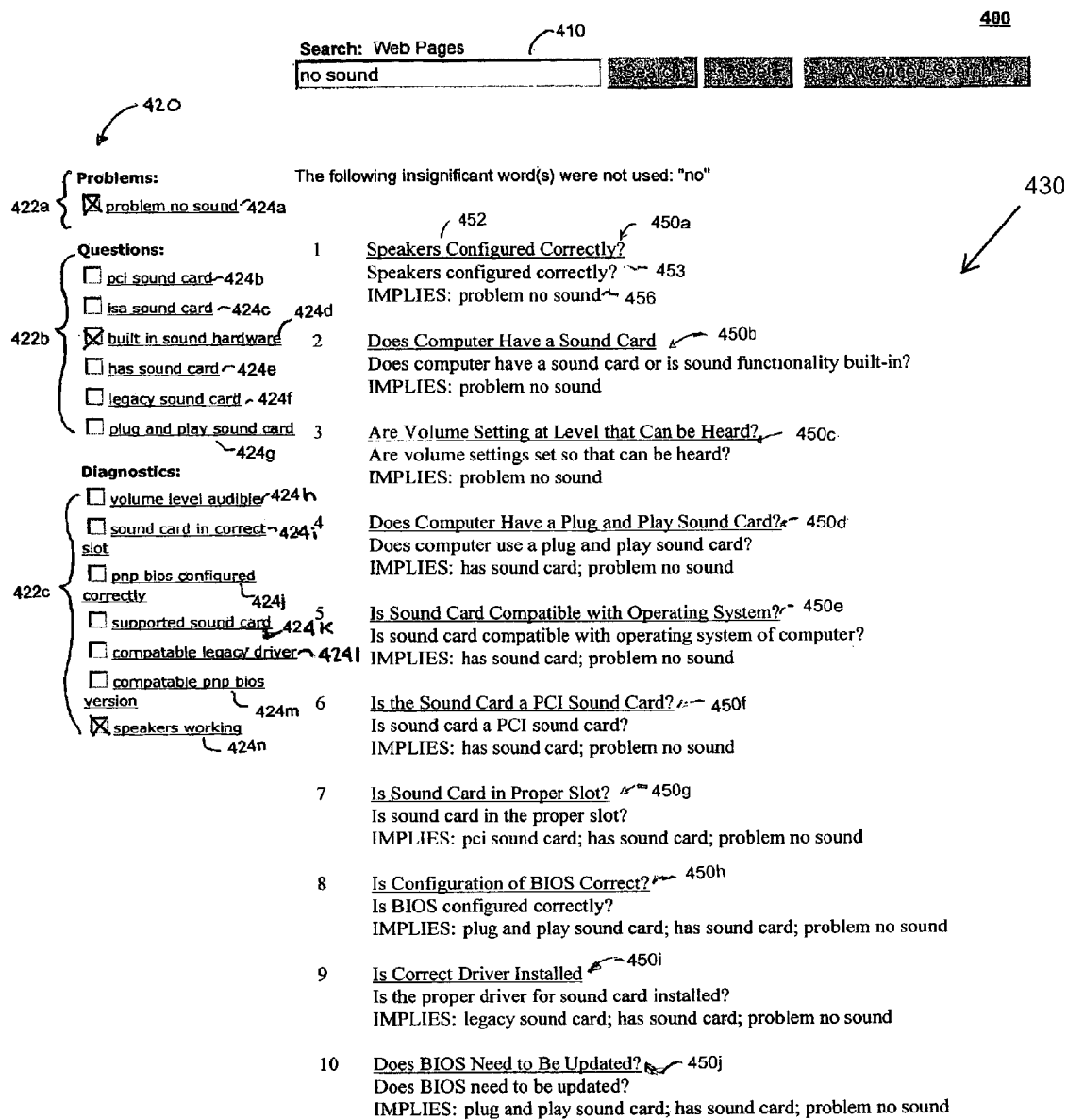
FIG. 4 depicts an exemplary screen shot of a decision support system result window, according to an embodiment of the present invention.

FIG. 2B depicts an exemplary node 250, according to an embodiment of the present invention. Node 250 includes a type field 251, a title field 252, an optional short description field 253, a detailed description/explanation field 254, an answer portion 255, a phrase portion 256, an optional success count 257, an optional author identification field 258, and an optional topic portion 259. A subset of the information associated with a node is displayed in a list presented to the user. An exemplary potential list 430 is shown in FIG. 4. In addition, each node has a separate node display page. Exemplary node display pages are shown in FIGS. 5 and 6. A subset of the information associated with a node is displayed on the node's display page.

Type field 251 stores the type indicator for the solution node. In an embodiment, node types include questions and diagnoses. As would be appreciated by a person of skill in the art, other types of nodes could be defined, as required.

Title field 252 stores the title of the node. The title is displayed in the list entry and on the individual node display page. Short description field 253 stores an abbreviated description of the node content. This field is optional. In an embodiment, short description field 253 is displayed in the list of nodes potentially related to the problem and not on the individual node display page. Detailed description field 254 includes a detailed discussion of the question, diagnosis, or remedy. In an embodiment, detailed description field 254 is displayed on the individual node display page.

Answer portion 255 includes one or more possible responses to the information presented in detailed description field 254. An input mechanism (e.g., a radio button or checkbox) is associated with each possible response. The input mechanism allows a user to select which response is "true" in the context of the presented information. In an embodiment, a response indicating that the node should be skipped or that the user does not know the appropriate answer may be included in answer portion 255. For example, a response "skip this and try something else" may be included. Answer portion 255 is generally displayed on the individual node page.

In a diagnosis node, responses are used to indicate whether the presented remedy or diagnosis was correct. In an embodiment, a diagnosis node presumes that the diagnosis or remedy presented may be correct. To facilitate processing, the response representing the presumption may be tagged separately. An additional presumed response field may be included in solution node 250. The response representing the presumption is stored the presumed response field.

Phrase potion 256 includes one or more phrases associated with node 250. A phrase is a descriptive set of words which are coherent in the context of the solution domain. In general, phrases create logical relationships among nodes. Each node asserts its validity based upon the user selected response values for other nodes. These dependencies are specified in phrase portion 256 as phrases.

In an embodiment, a phrase can be a problem phrase, a question phrase, or a diagnostic phrase. A problem phrase describes a specific problem in the domain that may be experienced by a user. In the domain of computer hardware, example problem phrases include "no sound," "sound distorted," or "sound has lapses." A question phrase identifies a characteristic of the problem domain. In the domain of computer hardware, example question phrases include "PCI sound card," "ISA sound card," "built-in sound hardware," or "has sound card." In an cell phone domain example question phrases may include a list of manufacturers or a list of model numbers. A diagnostic phrase describes a diagnostic attribute of a problem that may be experienced by a user. Example diagnostic phrases include "speakers in correct plug," "sound card in correct slot," "machine plugged in," or "speakers working." As would be appreciated by a person of skill in the art, other types of phrases could be defined in the present invention.

Phrases may optionally be displayed in the node list entry for a node. Typically, phrases are not displayed on an individual display node.

Success counter 257 is optional. When present, it stores the number of times the node was identified by a user as providing the correct diagnosis or solution to their problem. Each time a node solves a user's problem, the success counter is incremented. This allows the most common solutions for a problem to be ranked closer to the top of the potential node list for earlier evaluation.

Author identification (ID) field 258 stores an identifier associated with the author or creator of the solution node. Author ID field 258 is optional. In an embodiment, author ID field 258 is not displayed in the solution list entry or on the individual solution node display page.

Topic portion 259 is optional. When present, topic portion 259 includes one or more topics associated with a node 250. Topics are primarily used to optimize identification of the list of nodes potentially related to the problem, as described below. In an embodiment, topics are not displayed in the node list entry or on the individual node page.

2. Decision Support Processing

Figure 3:
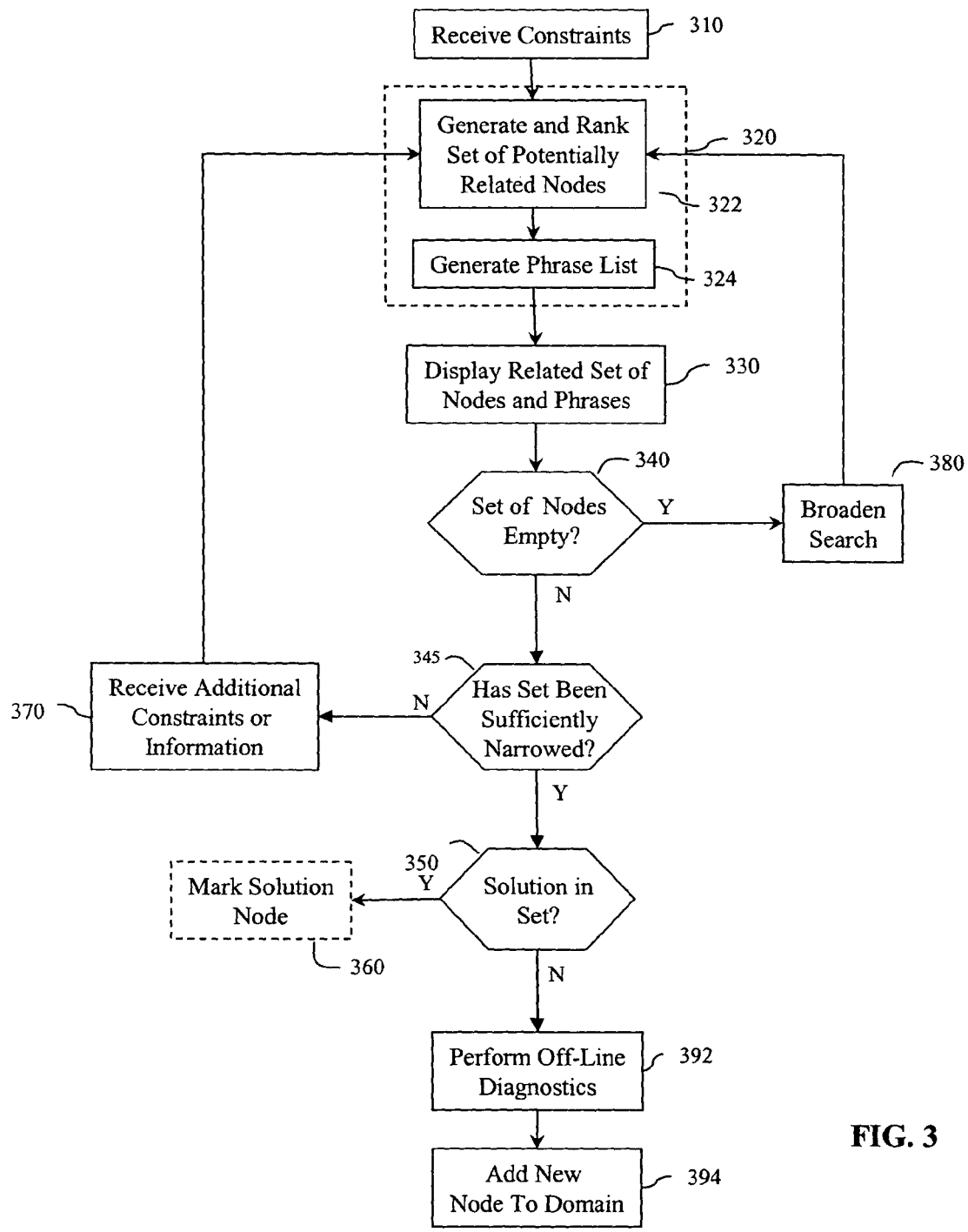
FIG. 3 is a flowchart illustrating an exemplary method for providing decision support, according to an embodiment of the present invention.

To identify a solution to a specific problem in a domain, a user performs an investigation process using decision support system 130. FIG. 3 is a flowchart 300 illustrating an exemplary method for providing decision support, according to an embodiment of the present invention. Flowchart 300 will be described with continued reference to the exemplary embodiment shown in FIG. 1 and exemplary solution node illustrated in FIG. 2B.

However, the invention is not limited to those embodiments. Note that some steps shown in flowchart 300 do not necessarily have to occur in the order shown. Although flowchart 300 is described with reference to troubleshooting applications, a person of skill in the art will recognize that the method can be applied to any decision support or similar application.

Flowchart 300 begins at step 310 when one or more constraints are received. FIG. 4 depicts an exemplary screen shot of a decision support system result window, according to an embodiment of the present invention. In step 310, one or more words or phrases descriptive of the problem being encountered are entered into constraint entry portion 410 of display window 400. The entered constraints represent the user's understanding of the problem being encountered. No limitation exists on the type, language, or format of terms to be used for constraints. In the exemplary screen shot of FIG. 4, a user has entered "no sound" as a constraint.

In step 320, a search of the nodes in the domain is performed. Step 320 includes step 322 and step 324.

In step 322, a set of nodes potentially related to the user's problem is generated and ranked. In an embodiment of the invention, the ranking of potentially related nodes is performed without using probabilities. The ranked node set is referred to as a list of potentially related nodes. The list includes nodes which have a greater than zero probability of being appropriate for the user-defined problem. A method for generating the list of potentially related nodes is described in detail below in Section 2.1.

In step 324, a phrase list is generated and ordered. The phrase list provides a mechanism for a user to enter additional information associated with the specified problem. A method for generating and ordering the phrase list is described in detail below in Section 2.2.

In step 330, a listing of the set of nodes potentially related to the user's problem and phrase list are displayed to the user. As depicted in FIG. 4, phrase list 420 is displayed on the left and potentially related set of nodes list 430 is displayed on the right. In an embodiment, phrase list 420 is divided into one or more phrase categories 422a-n based on the phrase types supported. For example, phrase list 420 may include a problem category 422a, a question category 422b, and a diagnostics category 422c. Each phrase category 422 includes any number of phrases 424 including zero.

The list of the set of potentially related nodes 430 includes any number of node entries 450 including zero. Each list entry 450 includes a node title 452, an optional short description 453, and one or more phrases 456. In an embodiment, one or more fields in a list entry 450 are linked to the individual node display for that node.

In step 340, a determination is made whether set of nodes potentially related to the user's problem is empty. If the set is empty, operation proceeds to step 380. If the set is not empty, operation proceeds to step 345.

In step 345, a determination is made whether the set of potentially related nodes has been sufficiently narrowed. If the set has been sufficiently narrowed, operation proceeds to step 350. If the set has not been sufficiently narrowed, operation proceeds to step 370.

In step 350, a determination is made whether any node in the set of potentially related nodes remedies the end user's problem. To make this determination, a user accesses one or more individual node pages. For example, a user may start with the first list entry and proceed in order through the listed nodes. If the solution is included in the list of potentially related solution nodes, operation proceeds to step 360. If the solution is not included in the list, operation proceeds to step 392.

FIG. 5 illustrates an exemplary screen shot of a diagnostic node display page 500. Diagnosis node 500 presents, for example, a potential remedy to a sound problem caused by a misconfigured plug & play BIOS. The detailed explanation section 554 describes what the problem with the plug and play BIOS could be and the steps the user can take to properly configure the plug and play BIOS. In answer portion 555, a user can enter a response indicating whether the solution was true. That is, whether the plug and play BIOS was misconfigured. If the plug and play BIOS was not misconfigured, the user can also enter that information into answer portion 555. The information entered into answer portion 555 then becomes a user-specified phrase if another iteration of searching is performed. Alternatively, answer portion 555, provides a user with the option of skipping this solution and trying another solution from the list. Note that although a "true" response may be asserted in the diagnosis node, the node may still not solve the end-users specific problem.

In step 360, the node is marked as a successful solution to the user's problem. This step is optional. When the solution is marked as successful, the success counter 257 for that node is incremented.

In step 370, one or more additional constraints or information is received. Additional constraints and/or additional information can be entered through a variety of different methods. In an embodiment, a user can enter additional constraint words into constraint entry portion 410.

Additionally, referring to FIG. 4, information can be entered via phrase list 420. As shown in FIG. 4, each phrase 424 has an associated indicator 426. Indicator 426 can be a check box, radio button, or similar mechanism to indicate selection of the associated phrase. A user can select one or more phrases 424 via their associated indicators 426. For example, a help desk worker can select any symptoms, configurations, observations or the like from the phrase list based on discussions with the end-user. Thus, the end-user identifies attributes associated with the problem without having to go through a sequence of steps which may involve answering questions that are unrelated to the problem being addressed.

As shown in FIG. 4, the user has selected three phrases "problem no sound" 424a, "built in sound hardware" 424d, and "speakers working" 424n. The selection is indicated by an X in the indicator box associated with the phrase.

Additional information can also be added via the answer portion on an individual solution node display pages. For example, a user can open an individual solution node 450 by activating its associated link in the list of potentially related nodes.

FIG. 6 illustrates an exemplary screen shot of a question node display page 600. Question node 600 is designed to elicit additional information about the end-user's operating environment. Specifically, the node of FIG. 6 seeks to identify whether the end-user's sound card is a plug and play sound card. The detailed description portion 654 briefly describes how the end-user can determine whether his sound card is plug and play. In answer portion 655, a user can enter a response indicating the answer to informational query. For example, the user can indicate that his operating environment includes "a legacy sound card" or a "plug and play sound card." The information entered into answer portion 655 then becomes a user-specified phrase if another iteration of searching is performed. This allows the subsequent search to be better tailored to the end-user's problem. Alternatively, answer portion 655, provides a user with the option of skipping this solution and trying another solution from the solution list.

After the additional information or constraints are entered, method 300 proceeds from step 370 to step 320. The nodes are searched and re-ranked in step 320 based on the newly entered information or constraint. The subsequent search may return nodes which were not included in the prior set of potentially related nodes. That is, the repetition of step 320 does not necessarily only narrow the prior set of potentially related nodes. It is a new search using the received constraints and/or information. In an embodiment, a user can initiate the re-ranking process by activating a search button (or the like) on the display page.

Figure 7:
FIG. 7 depicts a screen shot of the revised and re-ranked potential list after additional information was entered by a user, according to an embodiment of the present invention.

FIG. 7 depicts a screen shot of a result page 700 including the revised and re-ranked listing of the set of potentially related nodes after additional information was entered by a user, according to an embodiment of the invention. As can be seen in FIG. 7, in one iteration, the list of potentially related nodes was reduced from 10 nodes (in FIG. 4) to two nodes. Node 450c was listed in FIG. 4 as a potentially related node. However, node 750j was not included in the set of potentially related nodes listed in FIG. 4.

Steps 320-370 are repeated until the set of potentially related nodes has been sufficiently narrowed.

Step 380 relates to options that can be pursued if the set of potentially related nodes is empty. In an embodiment, if the set is empty, a notation is displayed. For example, the notation "no results" may be displayed.

In step 380, the search is broadened. For example, the prior search performed could have been unnecessarily over-constrained. Therefore, a broader search may be successful in identifying the solution to the user's problem. Operation then returns to step 320.

In step 392, additional diagnosis is performed on the user's problem. Step 392 is performed when the user (e.g., help desk employee) believes that the solution to the problem is not included in any of the existing solution nodes. In an embodiment, a knowledge expert may be consulted in real-time. The knowledge expert works with the information identified during the decision support process (steps 310-380) and additional details received from interaction with the end-user customer. When a solution to the user's problem is identified, the knowledge expert or help desk employee may decide that the solution should be added to the system. Operation then proceeds to step 394.

In step 394, the identified solution is added to the solution domain. New nodes can be entered in real-time while the user and/or knowledge expert are working with the end-user customer. Additional details related to entering a new node to the domain are described below in Section 2.3.

In an embodiment, advertisements are presented to the user when the list of potentially related nodes and/or individual node pages are displayed. These advertisements may be related to information entered by the user or to the node selected. For example, referring to FIG. 7, result page 700 includes advertisement 710.

2.1 List of Potentially Related Nodes Selection and Ranking

As described above, each node in the system contains implied relationships to the state of the user's knowledge of the problem being experienced. Referring to FIG. 2B, these implied relationships govern the appropriateness of the node for the problem being solved. These implied relationships are represented as phrases 256 in a node 250.

A node is appropriate to display in the list of potentially related nodes, if and only if, the associated phrases are true. It is not important that all phrases be known or proven to be true. However, if any of the implied phrases are false, the solution node has zero probability of being useful to the user. Formally, this is the following logical implication relationship:

$$\text{Appropriate}(D_1) \rightarrow C_1 \& C_2 \& C_3$$

By Modus tollens:

$$!C_1 | !C_2 | !C_3 | \rightarrow \text{Appropriate}(D_1)$$

Where,
$D_1$=Appropriate solution node containing solution to the user's problem
$C_n$=A phrase or state that is related to the user's problem
$\rightarrow$=If Assertion 1 is true, then Assertion 2 is true
!=False or Boolean NOT or Inverse
|=Boolean OR
&=Boolean AND Note that Modus tollens is the formal name for indirect proof or proof by contrapositive. To aid in implementing this logic, inverses of each phrase are specified when a phrase is initially defined for the system. In an embodiment, these inverse phrases are stored in phrase dictionary 160. For example, the inverse of the condition "The computer has a sound card" is "The computer has built-in sound." The use of inverses creates a set of exclusive value conditions (e.g., "computer has sound card" and "computer has built-in sound). If one phrase in this set is known to be true, the other phrase in this set must be false. In this way, a variable that traditionally has a single value can be represented by a set having multiple values.

Figure 8:
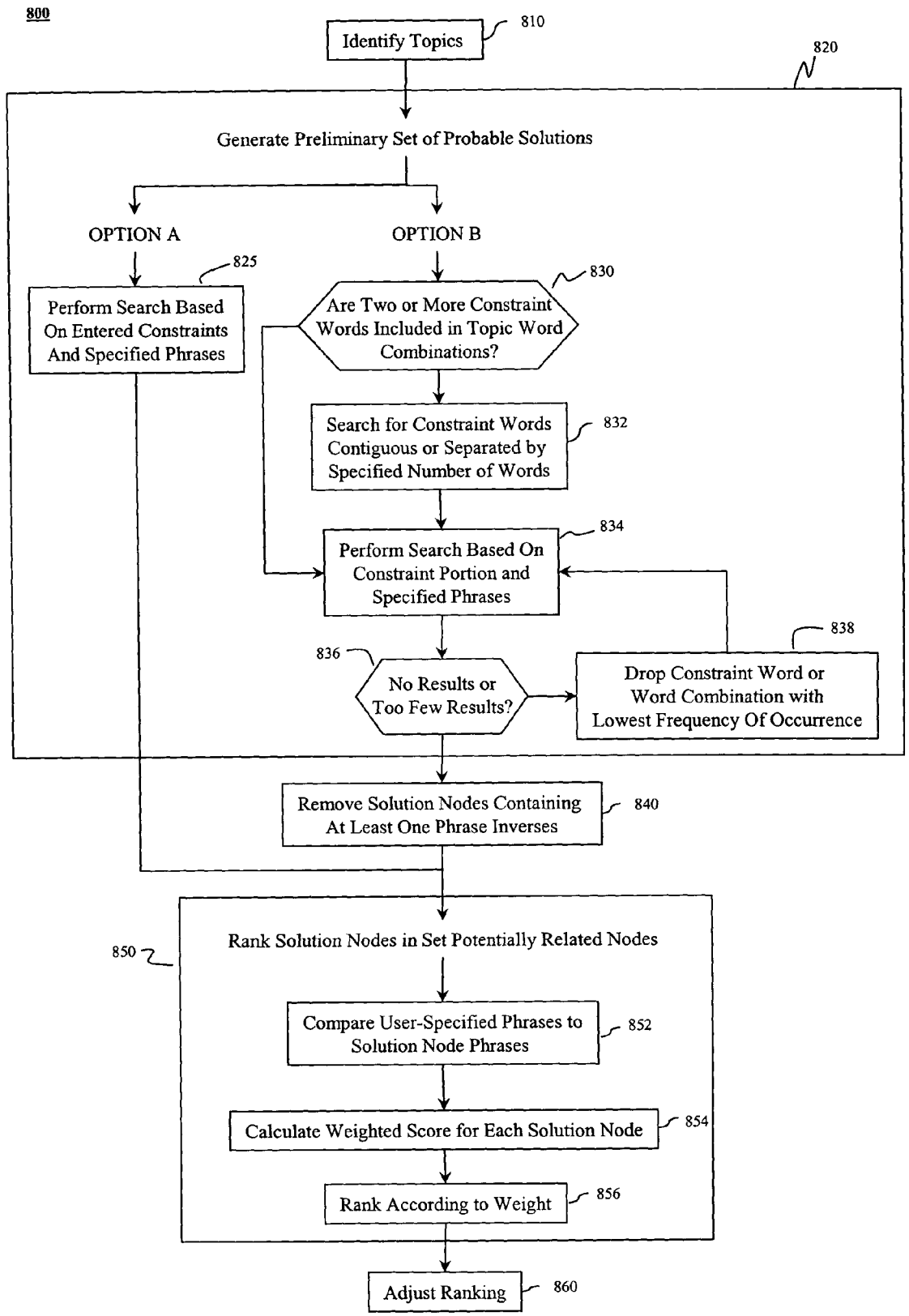
FIG. 8 is a flowchart illustrating an exemplary method for selection and ranking of the potential node set, according to an embodiment of the present invention.

FIG. 8 is a flowchart 800 illustrating an exemplary method for generating and ranking a set of nodes potentially related to a user's problem, according to an embodiment of the present invention. Flowchart 800 will be described with continued reference to the exemplary embodiment shown in FIG. 1 and the exemplary solution node shown in FIG. 2B. However, the invention is not limited to those embodiments. Note that some steps shown in flowchart 800 do not necessarily have to occur in the order shown.

In step 810, topics are identified for the nodes in the domain. This step is optional. The defined topics may be stored in topic list 172, in the individual solution nodes, or both. When present, in an embodiment, step 810 is not performed during the selection process. Instead, step 810 is performed when one or more nodes 250 are added to the decision support system. As described above, topics are words or word combinations that occur a statistically significant number of times in one or more solution nodes in the domain. For a more detailed description of identifying topics, see U.S. patent application Publication No. 2003/0167252, entitled "Topic Identification and User Thereof in Information Retrieval Systems", which is incorporated herein by reference in its entirety.

In step 820, a preliminary set of nodes potentially related to the user's problem is generated. A variety of options exist for generating the preliminary set of potentially related nodes. A first option, Option A, uses a basic search technique to select nodes. A second search option, Option B, uses topics to augment and facilitate searching. Decision support system 130 may include Option A, Option B, or both. In this embodiment, the option used is configurable by the system administrator. As would be appreciated by persons of skill in the art, other methods for generating the preliminary set of solution nodes may be used with the present invention.

Option A includes step 825. In step 825, the preliminary solution node set is selected from the nodes in the solution domain. The preliminary solution node set is selected using the entered "constraint" and the set of phrases previously identified by the user. In an embodiment, an OR based search pattern is used for the search. A solution node is part of the probable solution pool, if it contains the "constraint" OR it contains any of the identified phrases." Mathematically, this search clause can be represented as:

Contains (constraint OR $phrase_1$ OR $phrase_2$ ... OR $phrase_n$)

This search clause assures that a sufficient pool of nodes is returned for processing, even if the initial search constraint was slightly off target (e.g., over constrained).

Option B includes steps 830-838. In step 830, a determination is made whether 2 or more of the words entered as constraints are included in the topic list or in a node as a topic word combination. This step is optional. For example, if a user enters "no sound speakers" as a constraint, a determination will be made whether "no sound," "sound speakers," or "no sound speakers" are topics. If the constraint words are not included as topic word combinations, operation proceeds to step 834. If the constraint words are included as topic word combination, operation proceeds to step 832.

In step 832, a search clause having a constraint portion and a phrase portion is generated. The constraint portion is structured such that the constraint words which are topics are searched for contiguously or separated by a specified number of words in solution nodes. A node is a part of the set of potentially related nodes if it meets the constraint portion or contains any of the user-specified phrases.

In step 834, a search is performed using the generated search clause and the set of phrases previously identified by the user.

In step 836, a determination is made whether no results or too few results were returned as a result of the search. If no results or too few results were returned, the search of step 834 may be unnecessarily over constrained.

For example, this process may be used if multiple search terms were entered which caused the search to be over constrained. Operation then proceeds to step 838. If sufficient results were returned, operation proceeds to step 840.

During each iteration of steps 320-370 of the decision support process described in FIG. 3, one or more constraints are added to the search. In some circumstances, these additions lead to an over constrained search that will generally produce no potentially related nodes or too few potentially related nodes. Steps 836 and 838 provide a heuristic mechanism for managing such an over constrained search. In an embodiment, constraints are dropped based on their relevancy until a set of nodes that most accurately matches the problem constraints is produced.

In step 838, the least significant constraint word or word combination is dropped from the search. In an embodiment, the least significant constraint word is the word that has the highest frequency of occurrence. Frequency is the number of documents in which the word appears at least once. In an embodiment, a topic has associated frequency data. This frequency data is analyzed to determine the word or word combination that occurs a predetermined number times in a node or in the set of potentially related nodes. If a word or word combination is not listed as a topic, that word or word combination is assumed to have a low or zero frequency. In an embodiment, constraints related to search phrases are not dropped. In this way, if there are no matches, the user can identify that a new node needs to be added to the system.

Steps 834 through 838 are repeated until an appropriate preliminary solution node set is generated.

In step 840, any impossible or improbable solutions are removed from the solution pool. The resulting set of nodes is referred to as the set of potentially related nodes. In an embodiment, documents are removed from the solution pool using the Modus tollens logic, described above. In this embodiment, additional Boolean constraints are added to the search clause used in steps 825 or 834. For example, the following are added to the search clause:

AND DoesNotContain (inverse($phrase_1$))
AND DoesNotContain (inverse($phrase_2$))
.
.
.
AND DoesNotContain (inverse($phrase_n$))
Or more simply:
AND DoesNotContain (inverse($phrase_1$) OR inverse($phrase_2$) OR ... inverse($phrase_n$))

As would be appreciated by persons of skill in the art, removal clauses used in step 840 can be combined with the search clauses generated in step 820. For example, for the basic search of step 835, the resulting search clause may be represented as:

Contains (Constraint OR $phrase_1$ OR $phrase_2$ ... OR $phrase_n$)
AND
DoesNotContain (inverse($phrase_1$) OR inverse($phrase_2$) OR ... inverse($phrase_n$))

The search returns a set of nodes which have a greater than zero probability of being appropriate. Thus, all inappropriate nodes are filtered from the set of potentially related nodes.

For example, if a user enters the search constraint "No Sound" and also specifies the following phrases: "The computer has a sound card" and "The sound card is plug-and-play", the following search clause is used:

Contains ("No Sound" OR "The computer has a sound card" OR "The sound card is plug-and-play") AND NOT ("The computer has built-in sound" OR "Legacy sound card")

Note that the inverse of "The computer has a sound card" is "The computer has built-in sound" and the inverse of "The sound card is plug-and-play" is "Legacy sound card."

In step 850, the set of nodes potentially related to the problem generated as a result of steps 820 and 840 are ranked. Step 850 includes steps 852 through 856. Steps 852 through 856 are described with reference to the exemplary elements of the investigation depicted in FIG. 9.

In step 852, for each node in the set of potentially related nodes, the specified phrases are compared to the phrases 256 of each node 250. A phrase 256 which is also a specified phrase is considered "matched." A phrase which is not a specified phrase is considered "unmatched." For example, in FIG. 9, the two specified conditions 920a and 920b are compared to phrases of potentially related nodes 950 and 960. Phrases 952a and 952b of potentially related node 950 match specified conditions 920a and 920b, respectively.

These phrases are considered "MATCHED." Condition phrase 956c does not match any of the specified conditions. This phrase is considered "UNMATCHED."

In step 854, a weighted score for each node is calculated. In an embodiment, a first weighting function is multiplied by the number of matched phrases in the node to generate a matched value and a second weighting function is multiplied by the number of unmatched phrases in the node to generate an unmatched value. The unmatched value is then subtracted from the matched value to determine the weighted score. Mathematically, this can be represented by the following equation:

$$\text{Rank} = (k_1 * \text{ number of matched phrases in the solution node}) - (k_2 * \text{ number of unmatched phrases in the solution node})$$

In the example of FIG. 9, assuming $k_1$ has a value of 10 and $k_2$ has a value of 2, node 950 has a weighted score of 18 (10*2−2*1) and node 960 has a weighted score of 20 (10*2−2*0).

In step 856, the set of potentially related nodes are ranked according to their weighted score. The resulting ranked list is referred to as list of potentially related nodes. In the example of FIG. 9, node 960 would be displayed higher in the list of potentially related nodes than node 950.

As would be appreciated by persons of skill in the art, additional or alternative methods for ranking nodes could be used with the present invention. For example, an additional weight can be given to nodes which include the entered constraints in their title.

In step 860, the rankings of the potentially related nodes determined in step 850 are adjusted. This step is optional. In an embodiment, rankings are adjusted using the value of the success counter associated with the solution node. As described above, each time a node solves the user's problem, the solution success counter is incremented for that node. The use of the success counter to adjust rankings of potentially related nodes allows for the most common solutions to a problem to migrate to the top of the result list for earlier evaluation by the user. One method for adjusting rankings using the success counter is described in FIG. 10.

Figure 10:
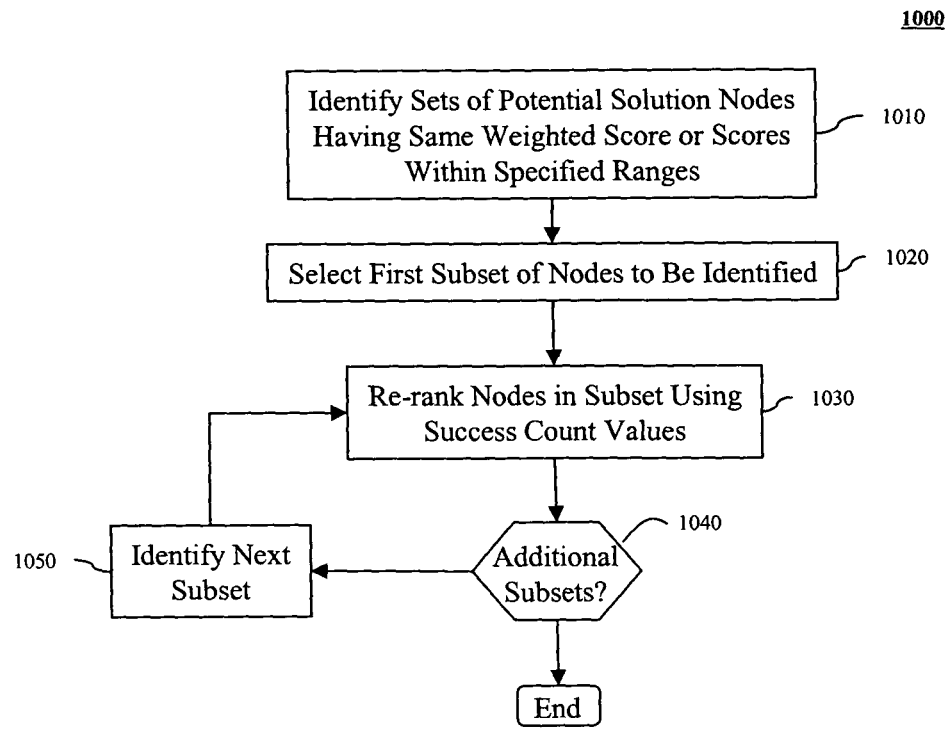
FIG. 10 is a flowchart illustrating an exemplary method for adjusting ranking using a success counter, according to an embodiment of the present invention.

FIG. 10 is a flowchart 1000 illustrating an exemplary method for adjusting ranking using the success counter, according to an embodiment of the present invention. Note that some steps shown in flowchart 1000 do not necessarily have to occur in the order shown.

In step 1010, subsets of potentially related nodes having the same weighted score or scores within specified ranges are identified. Note that if no subsets are identified during step 1010, flowchart 1000 ends.

In step 1020, the first subset of potentially related nodes having the same weighted score or scores within a specified range is selected from the subsets identified in step 1010. In an embodiment, the subset having the highest weighted score is selected in this step. As would be appreciated by persons of skill in the art, other methods for selecting one of the subsets from the subsets identified in step 1010 can be used with the present invention.

In step 1030, the identified subset of potentially related nodes is re-ranked according the value of the success counter for each node. In an embodiment, the nodes in the subset are re-ranked in descending order of success counter values. Note that the re-ranking order may be identical to the order of the nodes in the subset prior to re-ranking.

In step 1040, a determination is made whether any additional subsets of solution nodes remain to be re-ranked. If additional subsets remain to be re-ranked, operation proceeds to step 1050. If no additional subsets remain to be re-ranked, operation proceeds to step 1060 where flowchart 1000 ends.

In step 1050, the next subset is identified. Operation returns to step 1030.

Steps 1030-1050 are repeated until each identified subset is processed.

2.2 Phrase List Generation and Ordering

Figure 11:
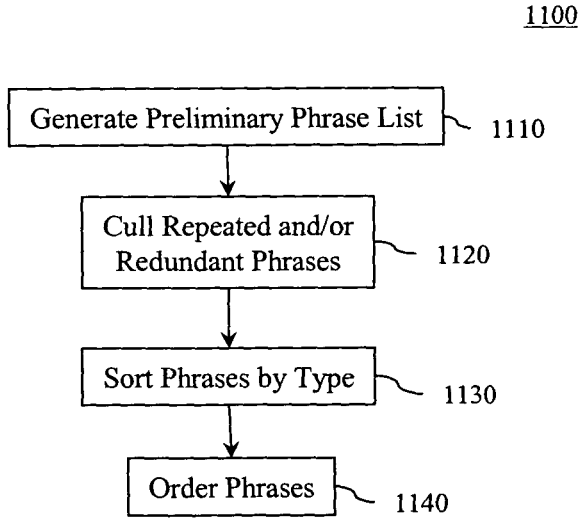
FIG. 11 is a flowchart illustrating an exemplary method for generating a phrase list, according to an embodiment of the present invention

FIG. 11 is a flowchart 1100 illustrating an exemplary method for generating a phrase list, according to an embodiment of the present invention.

Flowchart 1100 will be described with continued reference to the exemplary embodiment shown in FIG. 1 and exemplary screen shot of a result page shown in FIG. 4. However, the invention is not limited to those embodiments. Note that some steps shown in flowchart 1100 do not necessarily have to occur in the order shown.

Flowchart 1100 begins at step 1110 when a preliminary phrase list is generated by extracting phrases from each node in the set of potentially related nodes generated in step 320 of FIG. 3. As described above, each node has one or more phrases. Because a phrase may be associated with multiple nodes, the preliminary phrase list may include multiple instances of the same phrase and/or redundant phrases.

In step 1120, the redundant or repeat phrases are culled from the preliminary phrase list. The resulting phrase list is referred to as an interim phrase list. Note that steps 1110 and 1120 may be combined in an embodiment of the invention.

In step 1130, the phrases of an interim phrase list are sorted by category. This step is optional. As shown in FIG. 4, phrase list 420 includes three phrase categories: problems 422a, questions 422b, and diagnostics 422c. Each category may include any number of individual phrases 424, including zero. In an embodiment, if a category does not contain any phrases, the category is not displayed on the result page.

In step 1140, phrases are ordered. When step 1130 is present, phrases within each category are ordered. When step 1130 is not present, the interim phrase list is ordered. In an embodiment, phrases are ordered alphabetically. In an alternate embodiment, phrases are weighted and ranked according to their associated weight. As would be appreciated by person of skill in the art, other methods for ordering phrases can be used with the present invention.

2.3 Addition of a Node to a Solution Domain

Decision support system 130 provides a mechanism for rapidly integrating new nodes into a solution domain. Decision support system 130 can also be incrementally implemented. That is, individual nodes can be added one at a time and immediately integrated into a domain without disrupting the operation of the system.

In an embodiment, nodes are created through a node insertion feature.

In addition or alternatively, nodes are created using any standard text or HTML editor and automatically added using the appropriate search engine application. As would be appreciated by persons of skill in the art, other methods for creating solution nodes could be used with the present invention.

Figure 12:
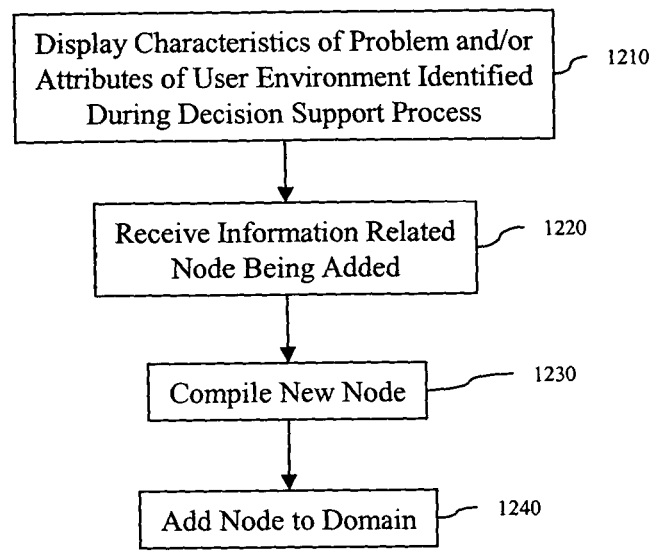
FIG. 12 is a flowchart illustrating an exemplary method for adding a node to a domain, according to an embodiment of the present invention

FIG. 12 is a flowchart 1200 illustrating an exemplary method for adding a node to a solution domain, according to an embodiment of the present invention. Flowchart 1200 will be described with continued reference to the exemplary screen shot of a node entry page shown in FIG. 13. However, the invention is not limited to that embodiment. Note that some steps shown in flowchart 1200 do not necessarily have to occur in the order shown.

Flowchart 1200 begins when a user or knowledge expert initiates the node insertion process after an initial investigation is performed using the method described in FIG. 3. The phrase selections made prior to this point identify the user's current situation and specify the cluster of currently known solutions that best fit the user's current situation. This prior analysis simplifies the clustering of new solution that better fits the user's situation. Upon initiating node insertion processing, a node entry window is displayed. An exemplary screen shot of a node entry page 1300 is depicted in FIG. 13.

In step 1210, the phrases and constraints specified by the user during decision support processing are displayed in a solution node entry window. As shown in FIG. 13, the specified phrase list 1330 is displayed on the left side of the window.

In step 1220, information related to the new node is received. As described above in reference to FIG. 2, each node includes a set of mandatory and optional data. This data is entered by a user and transmitted to the system 130 in step 1220. As shown in FIG. 13, node entry window includes multiple fields into which a user can enter information related to the new node. As described above, solution entry window includes a list of specified phrases. Each phrase 1332 includes an associated indicator 1334. The phrase indicator allows the user to select which phrases apply or to deselect those phrases which do not apply. For example, during the initial decision support processing, a number of phrases may have been identified that were relevant to the user's immediate situation but were not relevant to the ultimate solution to the problem. The user may uncheck these phrases prior to adding the node to the domain.

Node entry window further includes a title field 1320, a short description field 1335, and a detailed description field 1340. The title for the node is entered into title field 1320. An abbreviated description of the node content is entered into short description field 1335. A detailed discussion of the question, diagnosis, or remedy is entered into detailed description field 1340.

Node entry window also includes a type entry field 1360. Type entry field 1360 is a mechanism for specifying what type of node is being entered (e.g., question or diagnosis). The exemplary type entry field 1360 shown in FIG. 13 includes a single type field and an indicator. In this example, if the indicator is selected, the node is defined as a question node. If the indicator is not selected, the node is defined as a diagnosis node. As would be appreciated by persons of skill in the art, other mechanisms for identifying the node type could be used.

Node entry window also includes a phrase entry portion 1350. The phrases on the left identify how the newly entered solution relates to or clusters with the existing solutions. Their state represents the relevant user situation that led to the user's current problem. In addition to the phrases selected on the left, the user may feel that additional phrases should be associated with the new solution node. These phrases identify how this particular solution is differentiated from previously entered solutions. These two additional phrases (positive and negative statements) are always required. These phrases become the cluster points that future solutions will use to cluster with, and differentiate from this solution.

Phrase entry portion 1350 includes one or more entry fields to allow the user to enter phrases. In an embodiment, the phrases are selected from the list of phrases already defined in the system. Additionally, a user or knowledge worker may add a new phrase to the system. When a new phrase is added to the system, the phrase inverse is specified. The new phrase and its associated inverse are stored in phrase dictionary 160.

Node entry window may also include a page identifier field 1310. The page identifier 1310 uniquely identifies the page within the decision support system. In an embodiment, the page identifier 1310 is automatically assigned by the system when the node entry window is accessed. Additionally or alternatively, the page identifier 1310 may be entered manually by the user.

In step 1230, the new node is compiled. Step 1230 places node in the proper format for use by decision support system 130. For example, step 1230 may be initiated when the user activates an "insert" button or the like on the node entry window. Step 1230 includes determining whether all the required information has been entered into the node entry fields and whether the syntax of the entries is correct. During step 1230, author identification and topic information may be determined for the solution node.

In step 1240, the node is integrated into the domain.

3. Conclusion

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A method for identifying a set of related diagnoses and questions related to a problem in a solution domain having a plurality of nodes, comprising:

receiving a constraint at a computing device;

searching, by the computing device, the plurality of nodes to generate a first set of related nodes, wherein each node in the first set of related nodes includes:

at least a portion of the constraint;

a phrase comprising a diagnosis, a problem statement, or a question;

a response to the phrase;

a type indicator indicating whether the phrase is a diagnosis, problem statement, or a question; and a success counter configured to store a running count of the number of times the respective node has been chosen as a solution to the problem;

generating a first phrase list at the computing device, wherein the first phrase list includes one or more of the phrases contained within at least some of the first set of related nodes, each phrase in the first phrase list being selectable;

receiving, at the computing device, a selection of one or more phrases from the first phrase list; and searching, by the computing device, the plurality of nodes to generate a second set of related nodes, wherein each node in the second set of related nodes includes any of the one or more phrases selected, and wherein the success counter is used to weight a ranking of the respective node in the second set of related nodes.

2. The method of claim 1, wherein the first phrase list comprises a first phrase to include a question relating to the constraint, a second phrase to include a diagnosis relating to the constraint, and a third phrase to include a problem statement relating to the constraint.

3. The method of claim 1, wherein each node includes a plurality of responses to information presented in the node.

4. The method of claim 3, wherein the one or more phrases include at least one of the plurality of responses in a node.

5. The method of claim 1, wherein each node further comprises:
a short description;
an author identification;
a title; and
one or more topics that relate to the node.

6. The method of claim 5, wherein generating a first phrase list comprises:
retrieving the one or more phrases from a node in the first set of related nodes to generate a first set of phrases;
removing redundant phrases from the first set of phrases to generate a second set of phrases; and
ordering the second set of phrases.

7. The method of claim 6, wherein ordering the second set of phrases comprises ordering the phrases alphabetically.

8. The method of claim 6, further comprising separating the second set of phrases into one or more categories.

9. A method for identifying a set of diagnoses and questions related to a problem in a solution domain having a plurality of nodes, comprising:
receiving, at a computing device, a constraint comprising one or more phrases;
searching, by the computing device, the plurality of nodes to generate a first set of related nodes, wherein the search selects nodes that include the constraint;
generating a phrase list at the computing device, wherein the phrase list includes one or more phrases contained within the first set of related nodes, each phrase being selectable;
receiving, at the computing device, a selection of one or more phrases from the first phrase list;
removing, by the computing device, nodes from the first set of related nodes that include an inverse of the phrases selected from the first phrase list to generate a second set of related nodes; and
ranking, by the computing device, the nodes in the second set of related nodes, wherein ranking the nodes in the second set of related nodes comprises:
determining, by the computing device, the number of phrases that match any of the one or more phrases;
determining, by the computing device, the number of phrases that do not match any of the one or more phrases;
multiplying, by the computing device, the number of matched phrases by a first weight to generate a matched value;
multiplying, by the computing device, the number of unmatched phrases by a second weight to generate an unmatched value;
subtracting, by the computing device, the unmatched value from the matched value to generate a weighted score for the node; and
incrementing, by the computing device, a success counter associated with a node when the node is identified as a proper diagnosis of the problem, wherein the success counter is used to further weight the ranking of the respective node in the second set of related nodes.

10. The method of claim 9, wherein ranking the nodes in the second set of related nodes further comprises ranking the nodes in the second set of related nodes in ascending or descending order of weighted scores.

11. The method of claim 9, further comprising:
adjusting the ranking of the nodes in the second set of related nodes using a success counter associated with each node in the second set of related nodes.

12. The method of claim 9, further comprising:
prior to receiving a constraint generating topics associated the plurality of nodes in the solution domain, wherein a topic is a word or word combination that occurs a statistically significant number of times in a node.

13. The method of claim 12, further comprising:
determining whether the constraint includes a word combination that is a topic.

14. The method of claim 13, wherein if the constraint includes a word combination that is a topic, searching the plurality of nodes to generate the first set of related nodes comprises selecting nodes that include the words in the word combination of the constraint contiguously.

15. The method of claim 13, wherein if the constraint includes a word combination that is a topic, searching the plurality of nodes to generate the first set of related nodes comprises selecting nodes that include the words in the word combination of the constraint separated by a specified number of words.

16. The method of claim 12, further comprising:
determining the frequency that each topic occurs within a node.

17. The method of claim 16, further comprising:
if the second set of nodes is empty, comparing each word and word combination in the constraint to the topics;
determining the frequency of occurrence for each word and word combination in the constraint;
modifying the constraint to remove the word or word combination having the lowest frequency of occurrence; and
searching the plurality of nodes to generate a third set of related nodes.

18. The method of claim 9, further comprising:
if the second set of related nodes is empty, investigating the problem off-line to identify a diagnosis for the problem;
entering a new node to the domain, wherein the new node includes the diagnosis identified for the problem; and
integrating the new node into the domain.

19. A computer-readable medium having instructions thereon that, if executed by a computing device, cause the computing device to perform operations comprising:
receiving a constraint;
searching the plurality of nodes to generate a first set of related nodes, wherein each node in the first set of related nodes includes:
at least a portion of the constraint;
a phrase comprising a diagnosis, a problem statement, or a question;
a response to the phrase;
a type indicator indicating whether the phrase is a diagnosis, problem statement, or a question; and
a success counter configured to store a running count of the number of times the respective node has been chosen as a solution to the problem;
generating a first phrase list, wherein the first phrase list includes one or more of the phrases contained within at least some of the first set of related nodes, each phrase in the first phrase list being selectable;

receiving a selection of one or more phrases from the first phrase list; and searching the plurality of nodes to generate a second set of related nodes, wherein each node in the second set of related nodes includes any of the one or more phrases selected, and wherein the success counter is used to weight a ranking of the respective node in the second set of related nodes.

20. A computer-readable medium having instructions thereon that, if executed by a computing device, cause the computing device to perform operations comprising:

receiving a constraint comprising one or more phrases;

searching the plurality of nodes to generate a first set of related nodes, wherein the search selects nodes that include the constraint;

generating a phrase list, wherein the phrase list includes one or more phrases contained within the first set of related nodes, each phrase being selectable;

receiving a selection of one or more phrases from the first phrase list;

removing nodes from the first set of related nodes that include an inverse of the phrases selected from the first phrase list to generate a second set of related nodes; and ranking the nodes in the second set of related nodes, wherein ranking the nodes in the second set of related nodes comprises:

determining the number of phrases that match any of the one or more phrases;

determining the number of phrases that do not match any of the one or more phrases;

multiplying the number of matched phrases by a first weight to generate a matched value;

multiplying the number of unmatched phrases by a second weight to generate an unmatched value;

subtracting the unmatched value from the matched value to generate a weighted score for the node; and incrementing a success counter associated with a node when the node is identified as a proper diagnosis of the problem, wherein the success counter is used to further weight the ranking of the respective node in the second set of related nodes.

* * * * *

UNITED STATES PATENT AND TRADEMARK OFFICE
CERTIFICATE OF CORRECTION

| | | |
|---|---|---|
| PATENT NO. | : 8,433,711 B2 | Page 1 of 1 |
| APPLICATION NO. | : 11/222046 | |
| DATED | : April 30, 2013 | |
| INVENTOR(S) | : Odom et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1428 days.

Signed and Sealed this
Twenty-first Day of October, 2014

Michelle K. Lee
*Deputy Director of the United States Patent and Trademark Office*